US010391491B2

(12) United States Patent
Toner et al.

(10) Patent No.: US 10,391,491 B2
(45) Date of Patent: Aug. 27, 2019

(54) PLATELET-TARGETED MICROFLUIDIC ISOLATION OF CELLS

(71) Applicant: The General Hospital Corporation, Boston, MA (US)

(72) Inventors: Mehmet Toner, Charlestown, MA (US); Shannon Stott, Stoneham, MA (US); Eduardo Reategui, Revere, MA (US); Xiaocheng Jiang, Stoneham, MA (US)

(73) Assignee: The General Hospital Corporation, Boston, MA (US)

( * ) Notice: Subject to any disclaimer, the term of this patent is extended or adjusted under 35 U.S.C. 154(b) by 98 days.

(21) Appl. No.: 15/502,136

(22) PCT Filed: Aug. 7, 2015

(86) PCT No.: PCT/US2015/044375
§ 371 (c)(1),
(2) Date: Feb. 6, 2017

(87) PCT Pub. No.: WO2016/023008
PCT Pub. Date: Feb. 11, 2016

(65) Prior Publication Data
US 2017/0225166 A1 Aug. 10, 2017

Related U.S. Application Data

(60) Provisional application No. 62/034,522, filed on Aug. 7, 2014.

(51) Int. Cl.
*B01L 3/00* (2006.01)
*C12N 5/09* (2010.01)
*G01N 33/543* (2006.01)
*G01N 33/574* (2006.01)

(52) U.S. Cl.
CPC ...... *B01L 3/502761* (2013.01); *C12N 5/0694* (2013.01); *G01N 33/54366* (2013.01); *G01N 33/57488* (2013.01); *B01L 2200/0652* (2013.01); *B01L 2300/087* (2013.01); *B01L 2300/0864* (2013.01);
(Continued)

(58) Field of Classification Search
CPC ..... B01L 2200/0652; B01L 2300/0877; B01L 2400/086; B01L 3/502761; B01L 2300/0864; B01L 2300/087; B01L 2200/0668; B01L 2300/0822; B01L 2300/168; C12N 5/0694; C12N 2531/00; G01N 33/54366; G01N 33/56966; G01N 33/56972; G01N 33/57488; G01N 30/6095; G01N 33/574; G01N 2800/52; G01N 33/86; G01N 24/088; G01N 2333/515; G01N 24/08; G01N 2800/226; G01N 2800/222; G01N 33/6893; G01N 2333/185; G01N 2333/49; G01N 2333/503; G01N 2333/75; G01N 2800/224; G01N 2800/24; G01N 2800/368; G01N 33/4905; G01N 33/56983; G01N 33/57484; G01N 33/6872; G01N 2333/47; G01N 2333/4716; G01N 2333/5428; G01N 2333/55; G01N 2333/76; G01N 2800/26; G01N 2800/56; G01N 33/564; G01N 33/6851; G01N 33/6869; Y10S 436/824; Y02A 90/26; Y02A 50/53; G01R 33/448; G01R 33/465; A61B 5/02007; A61B 5/0263; A61B 5/7246; A61M 1/10; A61M 1/1086; A61M 1/12; A61M 1/122; A61M 2205/33; A61M 2205/3303; A61M 2230/20; A61M 2230/207; C12Q 1/56; G16H 50/20
See application file for complete search history.

(56) References Cited

U.S. PATENT DOCUMENTS

| | | | |
|---|---|---|---|
| 6,495,333 B1 | 12/2002 | Willmann et al. | |
| 8,585,971 B2 | 11/2013 | Huang et al. | |
| 8,807,879 B2 | 8/2014 | Toner et al. | |

(Continued)

FOREIGN PATENT DOCUMENTS

| | | |
|---|---|---|
| CN | 102656458 | 9/2012 |
| WO | WO 2006/108101 | 10/2006 |

(Continued)

OTHER PUBLICATIONS

European Search Report and Written Opinion in International Application No. 15829024.7, dated Nov. 30, 2017, 11 pages.
Li, "Platelet-lymphocyte cross-talk," Journal of Leukocyte Biology, Jan. 2008, 83: 1069-1078.
O' Flaherty et al., "Circulating tumour cells, their role in metastasis and their clinical utility in lung cancer," Lung Cancer, Apr. 2012, 76: 19-25.

(Continued)

Primary Examiner — Deborah K Ware
(74) Attorney, Agent, or Firm — Fish & Richardson P.C.

(57) ABSTRACT

Methods and systems for isolating platelet-associated nucleated target cells, e.g., such as circulating epithelial cells, circulating tumor cells (CTCs), circulating endothelial cells (CECs), circulating stem cells (CSCs), neutrophils, and macrophages, from sample fluids, e.g., biological fluids, such as blood, bone marrow, plural effusions, and ascites fluid, are described. The methods include obtaining a cell capture chamber including a plurality of binding moieties bound to one or more walls of the chamber, wherein the binding moieties specifically bind to platelets; flowing the sample fluid through the cell capture chamber under conditions that allow the binding moieties to bind to any platelet-associated nucleated target cells in the sample to form complexes; and separating and collecting platelet-associated nucleated target cells from the complexes.

20 Claims, 10 Drawing Sheets

(52) U.S. Cl.
CPC . *B01L 2300/0877* (2013.01); *B01L 2400/086* (2013.01); *C12N 2531/00* (2013.01)

(56) References Cited

U.S. PATENT DOCUMENTS

| | | | |
|---|---|---|---|
| 8,986,966 | B2 | 3/2015 | Toner et al. |
| 2006/0223178 | A1 | 10/2006 | Barber et al. |
| 2006/0252054 | A1 | 11/2006 | Lin et al. |
| 2008/0113358 | A1 | 5/2008 | Kapur et al. |
| 2009/0298067 | A1 | 12/2009 | Irimia et al. |
| 2009/0311267 | A1* | 12/2009 | Stoll .................. C07K 16/2896 424/145.1 |
| 2013/0209988 | A1 | 8/2013 | Barber et al. |

FOREIGN PATENT DOCUMENTS

| | | |
|---|---|---|
| WO | WO 2010/036912 | 4/2010 |
| WO | WO 2011/028905 | 3/2011 |
| WO | WO 2011/063416 | 5/2011 |
| WO | WO 2014/121204 | 8/2014 |

OTHER PUBLICATIONS

International Preliminary Report on Patentability in International Application No. PCT/US2015/044375, dated Feb. 7, 2017, 7 pages.
International Search Report and Written Opinion in International Application No. PCT/US15/44375, dated Nov. 5, 2015, 17 pages.
Ozkumur et al., "Inertial Focusing for Tumor Antigen-Dependent and -Independent Sorting of Rare Circulating Tumor Cells," Science Translational Medicine, Apr. 2013, 5(179): 179ra47.
European Communication in Application No. 15829024.7, dated Nov. 5, 2018, 6 pages.
Office Action in Chinese Application No. 201580054400.3, dated Mar. 8, 2019, 17 pages (with English translation).
Kohli et al, "Cell and nanomaterial-based approaches for diagnosis and chemotherapy of metastatic cancer cells," Diss. Massachusetts Institute of Technology, 2010, 63 pages.
Office Action in Japanese Application No. 2017-506779, dated Jun. 4, 2019, 5 pages (With English Translation).

* cited by examiner

PLATELET-TARGETED MICROFLUIDIC ISOLATION OF CELLS

CROSS-REFERENCE TO RELATED APPLICATIONS

This application is a 371 U.S. National of PCT Application No. PCT/US2015/044375, filed on Aug. 7, 2015, which claims priority from U.S. Provisional Application Ser. No. 62/034,522, filed on Aug. 7, 2014, the contents of both of which are incorporated herein by reference in their entireties.

STATEMENT AS TO FEDERALLY SPONSORED RESEARCH

This invention was made with Government support under 5-U01-EB012493-04 and EB002503-06A1 awarded by National Institutes of Health, and under 125929-PF-14-137-01-CCE awarded by American Cancer Society. The Government has certain rights in the invention.

TECHNICAL FIELD

This invention relates to the isolation of nucleated cells from fluids such as blood.

BACKGROUND

Metastasis, the spread and growth of tumor cells from the primary site to distant organs, represents the most devastating and deadly attribute of cancer and is responsible for 90% of cancer deaths. Although a systematic understanding of metastasis biology is yet to be established, there is a growing recognition of the importance of circulating tumor cells (CTCs) as metastasis-initiating cells, which will provide a potential accessible source for early diagnosis, characterization and monitoring of cancer progression. The reliable detection and non-invasive isolation of CTCs and other nucleated cells from the blood of cancer patients, however, remains technically challenging, not only because of their extremely rare presence (as low as one in a billion or more blood cells), but also due to the level of heterogeneity in biophysical and biochemical properties.

In terms of size, CTCs and other rare nucleated cells can be as small as 5 to 8 microns, e.g., the size of red blood cells, or 8 to 18 microns, which is about the same size as human white blood cells, or over 100 microns in the form of CTC clusters. In terms of surface chemistry, the expression of epithelial cell adhesion molecule (EpCAM), a biomarker that has been widely used to target CTCs and epithelial cells in general in positive-selection methods has exhibited a large variation between clinical samples and can also be significantly down-regulated with cancer progression as a result of the epithelial-mesenchymal transition (EMT). Furthermore, tumor cells have been reported to actively interact with host cells in the microenvironment, e.g., blood cells such as white blood cells and platelets, during the development of metastasis, which may make the detection and isolation of CTCs even more challenging.

SUMMARY

The present disclosure describes methods and systems of isolating platelet-associated nucleated target cells, such as circulating epithelial cells, circulating tumor cells (CTCs), circulating endothelial cells (CECs), circulating stem cells (CSCs), neutrophils, and macrophages, from sample fluids, e.g., biological fluids, such as blood, bone marrow, plural effusions, and ascites fluid, using binding moieties that specifically bind to platelets. The methods include flowing the sample fluid including the platelet-associated target cells, e.g., CTCs, through a chamber, e.g., a cell capture chamber, under conditions that allow the binding moieties to bind to any target cells, e.g., CTCs, e.g., platelet-coated CTCs, in the sample to form complexes; and then separating and collecting the target cells from these complexes, thereby isolating the target cells from the sample fluid.

In certain embodiments, the methods are performed using systems, for example, one- or two-stage microfluidic systems, designed to achieve platelet-targeted target cell capture. In some embodiments, the fluid, e.g., blood, sample can be first processed through a microfluidic debulking device to remove free, unbound platelets and red blood cells (RBCs) before the sample fluid passes through the cell capture chamber. The debulking device can include one or more arrays of microposts to implement hydrodynamic size-based sorting. The resulting sample fluid containing target cells and white blood cells (WBCs) can then be processed through the cell capture chamber functionalized with anti-platelet antibodies for high-throughput capture of platelet-associated target cells such as CTCs. In some embodiments, the cell capture chamber can include a mixing structure that enhances the interaction of any platelet-associated target cells in the sample fluid with the platelet antibodies. In some embodiments, such a mixing structure is embodied as a so-called "herringbone" micromixer.

In general, the disclosure features methods for isolating platelet-associated nucleated target cells, e.g., circulating epithelial cells, CTCs, CECs, CSCs, neutrophils, and macrophages, from a sample fluid as described herein. The methods include obtaining a cell capture chamber including a plurality of binding moieties bound to one or more walls of the chamber, wherein the binding moieties specifically bind to platelets; flowing the sample fluid through the cell capture chamber under conditions that allow the binding moieties to bind to any platelet-associated nucleated target cells in the sample to form complexes; and separating and collecting target cells from the complexes thereby isolating the target cells from the sample fluid.

In some implementations, the methods described herein can further include treating the sample fluid with a platelet inhibitor prior to flowing the sample fluid through the cell capture chamber, wherein the platelet inhibitor inhibits unbound platelets from adhering to other cells. For example, other cells can be platelets, red blood cells, and/or white blood cells. In various implementations, the platelet inhibitor can be theophylline, adenosine, dipyridamole, Argatroban, and/or prostaglandin I2.

In any of the embodiments described herein, the binding moieties can be antibodies that bind specifically to platelets.

In some implementations, the methods can further include selectively depleting unbound platelets from the sample fluid while maintaining platelet-associated nucleated target cells in the sample fluid before flowing the sample fluid through the cell capture chamber. For example, the platelet depletion can be performed in a microfluidic device that includes a channel containing an array of microposts to implement deterministic lateral displacement. For example, the microposts can be arranged in a plurality of rows, wherein the microposts are spaced apart within a row by a distance of about 30 to about 60 microns, e.g., about 35 microns to about 56 microns, subsequent rows are spaced apart from a previous row by a distance of about 5 microns to about 15 microns, e.g., about 5.6 microns to about 9.0 microns, and wherein the microposts in each subsequent row are offset laterally from microposts in a previous row by a distance less than the spacing between the microposts within the row.

In other implementations, the platelet depletion is performed in a microfluidic device using centrifugal or inertial forces, or both or by density gradient centrifugation.

In some embodiments, the cell capture chamber and the microfluidic device can be both located on a single substrate or they can be located on separate substrates and are in fluid connection via a conduit. In some implementations, the cell capture chamber includes a plurality of chevron structures on an internal surface thereof arranged to create microvortices within the sample fluid.

In some embodiments designed for selective removal of the target cells, the binding moieties are bound to nanostructures that include a first member of a binding pair, wherein one or more internal surfaces of the cell capture chamber are bound to a layer of gelatin functionalized with a plurality of second members of the binding pair, and wherein the nanostructures are bound to a top layer of the gelatin by a binding interaction of the first and second members of the binding pair. In some implementations of these methods, the platelet-associated nucleated target cells are bound to the nanostructures by the binding moieties and the platelet-associated nucleated target cells are isolated by releasing the nanostructures from the gelatin by melting the gelatin at an increased temperature. Alternatively, the target cells can be isolated by releasing the nanostructures from the gelatin by applying a localized shear stress to the gelatin layer or by using a light-targeted photothermal effect.

In another aspect, the disclosure features a systems, e.g., two-stage microfluidic systems, for isolating platelet-associated nucleated target cells such as CTCs from a sample fluid. These systems include a first chamber, a second compartment, and a conduit fluidly connecting the two compartments. In particular, the conduit fluidly connects the product outlet of the first chamber to the inlet of the second chamber.

In these systems, the first compartment includes a microchannel having an inlet, a waste outlet, a product outlet, and an array of microposts arranged between the inlet and the outlets, wherein the microposts are arranged in rows and spaced apart by a distance that enables red blood cells and unbound platelets to flow through the device to a waste outlet and to cause platelet-associated nucleated target cells to be laterally displaced by the array of microposts to a product outlet, wherein the microposts in each subsequent row are offset laterally from microposts in a previous row by a distance less than the spacing between the microposts within the row.

The second chamber includes a microchannel having an inlet and an outlet, wherein fluid flows from the inlet to the outlet through the microchannel, and a plurality of grooves defined in and arranged on an internal surface of one or more walls, floor, and ceiling of the microchannel to create microvortices within the sample fluid; and binding moieties fixed to at least one internal surface, wherein the binding moieties specifically bind to platelets. For example, the binding moieties can be antibodies that bind specifically to platelets.

In various implementations of these systems, the microposts are spaced apart within a row by a distance of about 30 microns to about 60 microns, e.g., about 35 microns to about 56 microns, and subsequent rows are spaced apart from a previous row by a distance of about 5 microns to about 15 microns, e.g., about 5.6 microns to about 9.0 microns. In different embodiments the first chamber and the second chamber are both located on a single substrate or they can be located on separate substrates and are in fluid connection via the conduit.

In some embodiments, the grooves in the second chamber include an apex and two arms connected to the apex to form a V-shape, and the grooves are arranged such that the sample fluid flows past the arms towards the apex.

In certain implementations of these systems, the binding moieties are bound to nanostructures that comprise a first member of a binding pair, wherein one or more internal surfaces of the second chamber are bound to a layer of gelatin functionalized with a plurality of second members of the binding pair, and wherein the nanostructures are bound to a top layer of the gelatin by a binding interaction of the first and second members of the binding pair.

As used herein, the term "binding moiety" means any molecule or agent that can adhere to a target such as a particle, molecule, or cell. Binding moieties include, for example, members of a ligand binding pair, antibodies, aptamers, or nucleic acid molecules. Some binding moieties bind specifically to a target molecule or agent, such as a receptor or a cell surface marker on a cell surface, and some bind non-specifically to a variety of targets that may share a common feature.

As used herein, the term "specific binding" means that a binding moiety binds selectively and preferentially to a particular target, such as a particle, molecule, or cell, e.g., to a molecule on the surface of a cell, in a sample including other particles or molecules.

Compared with prior CTC sorting techniques that rely on special biophysical and/or biochemical properties of cancer cells, the methods and systems described herein focus on active cell-cell interactions during cancer metastasis, which is not limited by the size, cancer type, or the expression level of tumor surface antigens. More importantly, the new methods and systems enable the isolation of a very special subpopulation of nucleated target cells, such as CTCs, which are correlated with high metastatic potential, but are difficult to target by other techniques, and thus provide valuable information for both early cancer diagnostics and a better understanding of how cancer spreads.

In particular, one benefit of the new methods and systems described herein is that they do not rely on specific biomarkers on the surface of the target cells. Many current techniques rely on the expression of epithelial cell adhesion molecule (EpCAM), a biomarker that has been widely used to target epithelial cells and CTCs in positive-selection methods. However, EpCAM expression varies widely between clinical samples and can also be significantly down-regulated with cancer progression as a result of the epithelial-mesenchymal transition (EMT). The present methods and systems overcome this difficulty with prior methods.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1A:
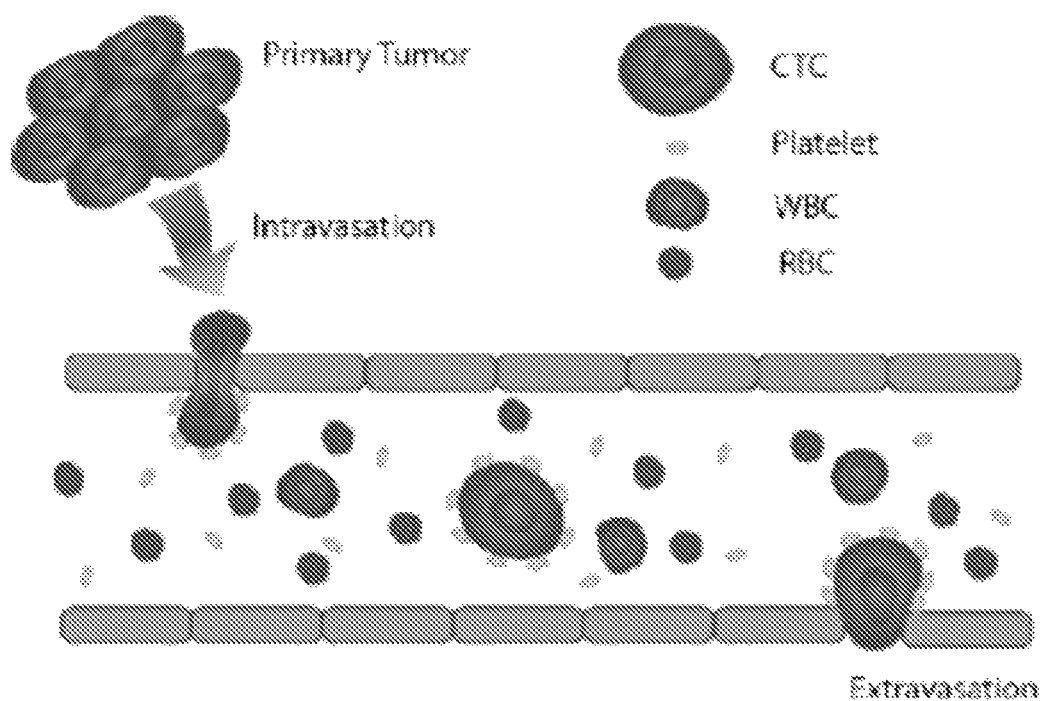
FIG. 1A is a schematic diagram of tumor metastasis via platelet-associated CTCs.

The interaction between tumor cells and platelets is thought to play a role in blood-borne metastasis, as shown schematically in FIG. 1A. The most compelling evidence is the inhibition of metastasis by platelet depletion and the restoration of metastatic potential by platelet reconstitution in several independent mouse studies. The unique capability of malignant tumor cells to activate and aggregate platelets on a surface, a process known as tumor cell-induced platelet aggregation (TCIPA), confers a number of advantages to the tumor in successful metastasis. The platelets might not only contribute to the vascular remodeling process in angiogenesis, but may also significantly enhance tumor cell survival in the bloodstream by shielding them against the shear stress and immune surveillance.

According to the new methods and systems described herein, a broad set of adhesion receptors on platelets can be used to isolate platelet-associated nucleated target cells, such as epithelial cells, CTCs, neutrophils, and macrophages from sample fluids such as blood, e.g., whole blood. In addition, recent research on the signaling between platelets and tumor cells revealed that the platelet-derived growth factors/cytokines help induce the epithelial-mesenchymal transition (EMT) and further enhance the metastatic potential. As a result, the new methods and systems are able to isolate CTCs that have an enhanced metastatic potential and can thus provide better diagnostic information than other CTCs that are not associated with platelets.

Methods of Isolating Target Cell-Platelet Clusters from Sample Fluids

The present methods and systems take advantage of the unique interplay between certain nucleated target cells, e.g., CTCs, and platelets and utilize platelets that are associated with such target cells, e.g., bound to, e.g., coated on, the surface of the target cells, as a ubiquitous, cell-based markers to target and isolate these target cells from sample fluids, such as blood, e.g., whole blood.

In general, the new methods use a chamber including a plurality of binding moieties bound to one or more walls of the chamber, wherein the binding moieties specifically bind to platelets; flowing the sample fluid including the target cells, if any, through the chamber under conditions that allow the binding moieties to bind to any platelet-associated target cells in the sample to form complexes; and separating and collecting target cells from the complexes thereby isolating the target cells from the sample fluid. Further, the methods can also include steps of selectively depleting unbound platelets and/or other contaminating cells, such as red blood cells (RBCs) from the sample fluid while maintaining platelet-associated target cells in the sample fluid before flowing the sample fluid through the chamber and/or using mixing in the chamber to enhance contacts between the platelets and the binding moieties.

Since TCIPA is a general phenomenon originating from the intrinsic interaction between tumor cells and host microenvironment, the platelet-targeted methodology has the potential to detect and isolate a broad spectrum of nucleated target cells in blood-borne metastasis independent of tumor membrane epitopes.

To reduce WBC contamination and improve CTC purity, platelet inhibitors can be added to the blood sample prior to testing to stabilize the blood. A variety of platelet inhibitors can be used, such as theophylline, adenosine, dipyridamole, Argatroban, and prostaglandin I2, for blood stabilization. A combination of EDTA with prostaglandin I2 is particularly effective at inhibiting the formation of platelet-leukocyte aggregates (PLA), and can reduce the number of contaminating WBCs in a blood sample by 90%.

Binding Moieties for Binding to Platelet-Associated Target Cells

Various binding moieties can be used to bind to the platelets in the sample fluid. For example, a variety of antibodies are known to target different platelet surface receptors, including CD41 and CD61 (subunits of integrin α2bβ3); CD42b and CD42c (the major receptors for von Willibrand factors (vWF); glycoprotein VI (GP VI) (the collagen receptor); and the thrombopoietin receptor (TPO-R). Of these anti-CD41 antibodies can be used effectively, as they have a high capture efficiency for platelets and low non-specific binding.

The binding moieties can be functionalized onto a solid support, such as PDMS or glass surfaces using various methods, such as silane chemistry. Different silane precursors with amine, aldehyde, or thiol terminal groups can be crosslinked with oxygen-plasma treated PDMS/glass surfaces, which can further be conjugated to different binding moieties. In a particular example, a solid support in the form of a microfluidic channel is modified with 3-mercaptopropyl tri-methoxy silane, followed by the addition of N-y-maleimidobutyryloxy succinimide ester as the linker, and finally conjugated to NeutrAvidin. Any biotinylated binding moieties, such as biotinylated platelet antibodies, can then be easily functionalized onto the device through avidin-biotin chemistry.

Flowing the Sample Fluid Through the Chamber with Binding Moieties

After surface functionalization, the devices are typically blocked with an agent to avoid non-specific binding, e.g., with a sufficient amount of bovine serum albumin (BSA), e.g., 3% BSA. Thereafter a specific volume, e.g., 1 to 10 mL, e.g., 2, 3, 4, 5, or 6 mL, of a sample fluid, e.g., blood, e.g., whole blood, or buffy coat, are flowed into the system. The sample fluids are typically processed at flow rates of 1-5 mL/hour, e.g., 1, 2, 3, or 4 mL/hour, at room temperature under a set pressure, e.g., 0.03 to 0.15 psi, e.g., 0.05, 0.075, or 0.1 psi.

Debulking the Sample Fluid to Remove Unbound Platelets

Because of the abundance of platelets in whole blood ($\sim 10^5/\mu L$) and the potential effect on saturating the binding moieties, the blood sample can be first processed to remove free, unbound platelets. In addition, it is helpful to remove some or most of the red blood cells (RBCs). The debulking can be accomplished, for example, with density gradient centrifugation or microfluidic-based cell separation.

Density gradient centrifugation is generally performed with blood samples collected in CPT tubes, which contain anticoagulant together with a polyester gel and a density gradient liquid. After centrifugation, the nucleated cells can then be harvested by carefully pipetting them from the liquid interface with minimal contamination from red blood cells and platelets.

The microfluidic-based blood debulking can be accomplished with different designs and techniques known in this field. For example, inertial forces can be utilized in curved, e.g., serpentine, microfluidic channels to differentially focus and sort cells based on their sizes by centrifugal or inertial forces (e.g., inertial focusing), or both (see, e.g., U.S. Pat. No. 8,807,879). In addition, hydrophoretic filtration and/or acoustic standing waves can also be utilized to sort cells of different sizes.

In another implementation, the unbound platelets can be removed from the sample fluid using a microfluidic debulking device. Such devices can be composed of one or more arrays of microposts to implement hydrodynamic size-based sorting, as described in further detail below. In general, these microfluidic debulking device uses hydrodynamic size-based sorting to achieve low shear microfluidic debulking of whole blood. RBCs, platelets, and plasma proteins are discarded, whereas nucleated cells (WBCs and CTCs) are retained and presented to the second stage for target cell, e.g., CTC, capture. The operational principle of microfluidic debulking is based on hydrodynamic size-dependent deterministic lateral displacement, in which coincident flow of cell-containing and cell-free solutions through an array of microposts leads to rapid size-based separation (see, e.g., U.S. Pat. Nos. 8,986,966 and 8,585,971). See also, Ozkumur et al., "Inertial Focusing for Tumor Antigen-Dependent and -Independent Sorting of Rare Circulating Tumor Cells," Science Translational Medicine, 5(179):179ra47 (DOI: 10.1126/scitranslmed.3005616) (2013).

By optimizing the array configuration (including the gap or space between the microposts and the shift between adjacent rows) and flow rate, one can achieve over a 5-log depletion of free, unbound platelets while maintaining most of the nucleated cells. The fluid product containing nucleated target cells and white blood cells (WBCs) can then be directed to the chamber that contains the platelet-specific binding moieties as described herein.

Mixing the Sample Fluid to Enhance Binding Interactions

To enhance the interaction of any platelet-associated target cells in the sample fluid with the binding moieties in the chamber, one can include a mixing structure within the chamber. For example, different channel structure designs, including zigzag, serpentine, or twisted channels, can be utilized for passive mixing. In addition, it is also possible to further enhance the mixing performance by incorporating active micro-mixing enabled by acoustic, pressure perturbation, or dielectrophoretic techniques.

One useful design is a so-called "herringbone" micromixer included on one or more of the internal walls, floor, or ceiling of the chamber functionalized with platelet antibodies for high-throughput capture of platelet-associated target cells such as CTCs (see, e.g., PCT Application No. WO 2010/036912). In general, 1-10 mL of a sample fluid, e.g., buffy coat or debulked blood, are flowed into the system. The sample fluid with continuous rocking was typically processed through the device at the flow rate of 1 to 2 mL/hr at room temperature under 0.03-0.15 psi, e.g., 0.05, 0.075, or 0.1 psi.

Processing the Target Cells Captured in the Chamber

All cells captured in the cell capture device can be processed for identification, e.g., with a staining assay, e.g., a four-color staining assay, for simultaneous target cell identification and platelet characterization. The captured cells that are positive for tumor markers (e.g., EpCAM, cytokeratin, epithelial growth factor receptor (EGFR), human epidermal growth factor receptor 2 (HER-2), cadherin-11, and 4',6-Diamidino-2-Phenylindole (DAPI)), and optionally those that are also negative for hematopoietic markers (such as CD45, CD14, CD16) are scored as CTCs. Reliable CTC capture can be achieved using the new methods with counts ranging from 0.4 to 8.5 CTCs/mL of whole blood samples. Other target cells can be identified using other markers. For example, epithelial cells can be detected with CD24, CD133, and CD326; neutrophils with CD15, CD16, and CD66b; and macrophages with CD11b, CD68, and CD163. In addition, circulating endothelial cells (CECs) can be identified with CD34 and CD146 and circulating stem cells (CSCs) can be identified with CD44, CD90, and ALDH1.

When CTCs are captured on microfluidic devices using prior techniques, e.g., devices functionalized with anti-epithelial marker antibodies, such as EpCAM antibodies, the results reveal consistently lower positive hits that then present methods. See FIG. 5, which as discussed in further detail in Example 2 below, shows that the cell capture systems described herein are capable of reliable capture of CTCs in the form of single cells or clusters from metastatic cancer patients with both epithelial (lung, breast) and non-epithelial (melanoma) tumor origins. The higher CTC counts from the present platelet-targeted approach are due, in part, to the new methods' capability to capture CTCs from the lung and other epithelial tumor types that might lose their epithelial nature and thus become more difficult to target by anti-epithelial marker antibodies, such as EpCAM antibodies.

Prior EpCAM-targeted approaches generally yield CTCs with limited associated platelets, while the CTCs captured using the new methods described herein exhibit a wide range of platelet coverage, including a special subpopulation of CTCs that were completely coated with platelets/fibrin. These platelet-coated CTCs have been hypothesized as high metastatic potential precursors because of platelet-enhanced tumor-cell survival and proliferation, but are very difficult to capture by conventional positive selection methods targeting tumor surface antigens. Quantitative imaging methods can be used to further investigate the correlation between CTC phenotype and platelet distribution. Combined with controlled cell release strategies that were recently developed by our group, it is also possible to achieve single-cell level genotypic studies that are expected to further advance our knowledge about cancer metastasis.

Once the platelet-associated CTCs are captured using the new methods, breast cancer CTCs can be identified using the same protocol as lung cancer samples, while melanoma CTCs are identified by staining with an antibody or antibody cocktail that targets melanoma specific antigens (e.g., any one or more of anti-CSPG4, MCAM, TYRP1, and α-SMA antibodies).

Purification of Captured Target Cells Through Selective Release

In some sample fluids such as whole aged blood there may be a large population of platelet-associated WBC cells that are isolated by the new methods along with the platelet-associated target cells.

In some embodiments, the new methods can include steps to selectively release target cells such as CTCs bound to the chamber that contains the binding moieties. For example, as described in International Application Publication No. WO 2014/121204, the cell capture chamber can include binding moieties that are bound to nanostructures that themselves include a first member of a binding pair, wherein one or more internal surfaces of the chamber are bound to a layer of gelatin functionalized with a plurality of second members of the binding pair, and wherein the nanostructures are bound to a top layer of the gelatin by a binding interaction of the first and second members of the binding pair. The target cells (bound via their associated platelets to the binding moieties bound to the nanostructures) can then be released from the chamber, via either of two release mechanisms.

In the first release mechanism, the target cells such as CTCs can be isolated and removed from the cell capture chamber by releasing the nanostructures from the gelatin by melting the gelatin at an increased temperature. By increasing temperature, e.g., over 30° C., e.g., 37° C., captured target cells can be released in a bulk fashion. Alternatively, in the second release mechanism, the target cells can be released from the gelatin by applying a localized shear stress the gelatin layer. By increasing a localized shear stress in the gelatin, e.g., by applying a frequency-controlled force with a vibrating device, e.g., a microtip device described, for example, in PCT WO 2014/121204 single cells can be selectively released from the cell capture chamber.

Figure 6:
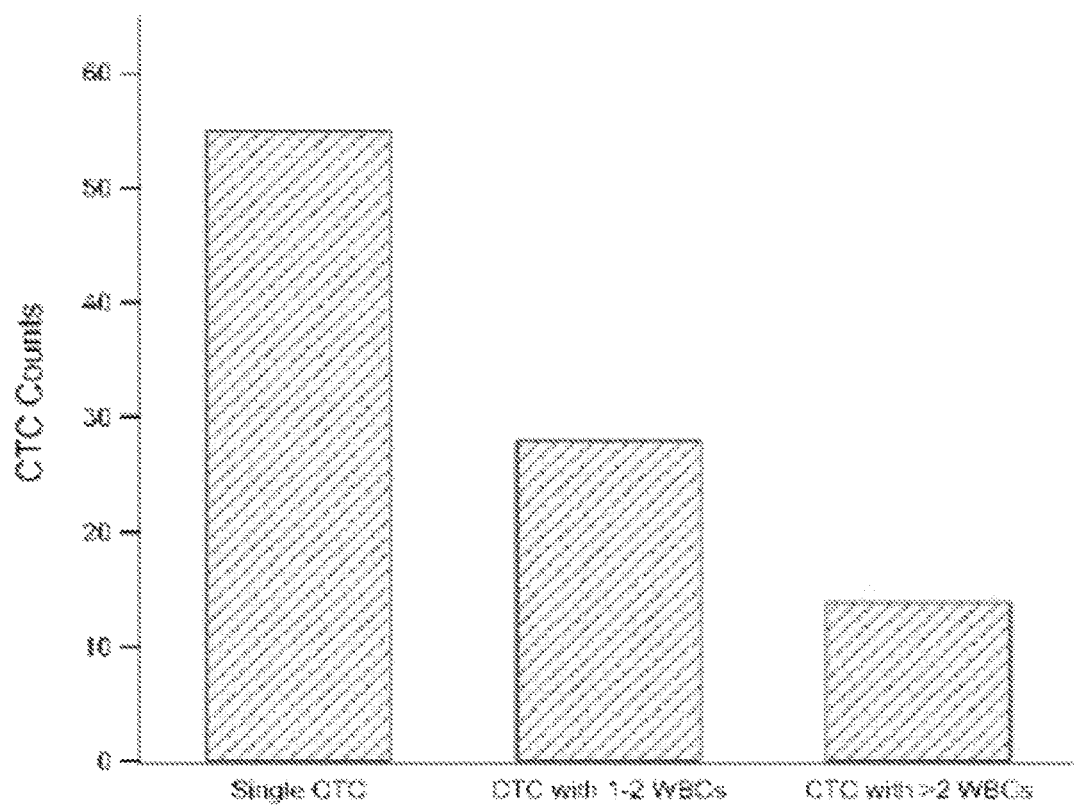
FIG. 6 is a graph showing counts of CTCs in the form of single cells, clusters of 1 or 2 WBCs, and clusters of greater than 2 WBCs.

In addition to single CTCs (about 55%), the new methods also isolate different sized cell clusters on the platelet-targeted platforms. Indeed over 40% of captured CTCs were in the form of CTC/WBC clusters. See FIG. 6, which shows that about 30% of CTCs were clustered with 1 or 2 WBCs, and about 15% of CTCs were clustered with more than 2 WBCs. The number of interacting WBCs increased with the platelet coverage around CTCs. The capability of the current approach to target both single CTCs and CTC/WBC clusters, the latter of which are very difficult to isolate through conventional affinity based positive or negative selection methods, would enable a comprehensive characterization of cancer metastasis through non-invasive blood biopsy, and also open up new opportunities in downstream applications, such as CTC culture, as a result of the improved CTC survival/proliferation in the specialized microenvironment.

The ability to isolate CTC/WBCs provides for isolation of a cell population that would otherwise be lost in other prior CTC isolation techniques. For example, negative-selection CTC isolation techniques target WBCs with magnetic material using antibody-based binding. In these methods, the magnetic particles are functionalized to bind specifically to WBCs and are introduced to the fluid sample prior to entering the microfluidic system. The fluid sample then enters a "deflection channel" subject to a magnetic gradient oriented to deflect the magnetic particles, and any cells bound to them, in a certain direction. When the fluid sample containing target cells/particles bound to one or more magnetic particles is introduced into a deflection channel, the magnetic force created by the nearby magnets pulls the magnetic particles (and the attached cells/particles) in a direction of the magnetic gradient. In the case of negative-selection CTC isolation, this separation diverts the WBCs, along with any other particles/cells attached to the WBCs, to the "waste" channel and isolates non-bound CTCs in the "product" channel. This method results in the loss of any CTCs bound to WBCs, which in turn, are bound to the magnetic particles, to the waste channel.

The two-stage microfluidic platforms described herein do not suffer from the same shortcomings.

Microfluidic Systems to Isolate Target Cells from Sample Fluids

As noted above, the methods for isolating platelet-associated nucleated target cells, such as CTCs, from sample fluids employ a cell capture chamber that contains a plurality of binding moieties bound to one or more walls, floor, and/or ceiling of the chamber, wherein the binding moieties specifically bind to platelets. The fluid sample including the target cells is flowed through the chamber under conditions that allow the binding moieties to bind to any platelet-associated target cells in the sample to form complexes. This process provides for the separation and collection of target cells, such as CTCs, from the complexes thereby isolating target cells from the sample fluid. Furthermore, as shown in FIG. 1B, the systems can include an upstream component (first stage 110) that selectively depletes unbound platelets and other cells, e.g., red blood cells (RBCs) from the sample fluid while maintaining platelet-associated CTCs in the sample fluid before flowing the sample fluid through the cell capture chamber (second stage 120).

Figure 1B:
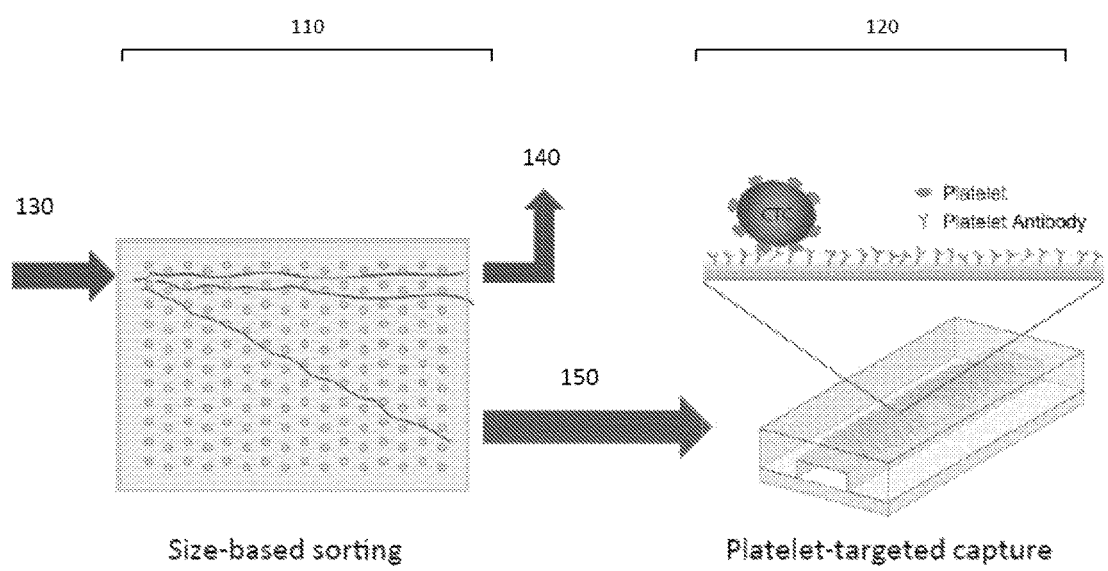
FIG. 1B is a schematic diagram of one embodiment of a two-stage microfluidic platform designed to achieve platelet-targeted CTC capture.

As shown in FIG. 1B, the input fluid to the system can be whole blood 130. The first stage 110 separates unbound platelets and other cells, e.g., RBCs, 140 from the nucleated cells (150) that continue through the system to enter the platelet-targeted capture chamber (120).

Stage One—Debulking Device to Remove Red Blood Cells and Platelets from Sample Fluid For the first stage, the overall system can include a debulking device 200, e.g., a microfluidic device composed of one or more arrays of microposts to remove RBCs and free platelets from whole blood through hydrodynamic size-based sorting that allows the smaller platelets and RBCs to exit the device as waste while passing the larger WBC and CTC and cell clusters to the second stage, which is the cell capture chamber.

Figure 2A:
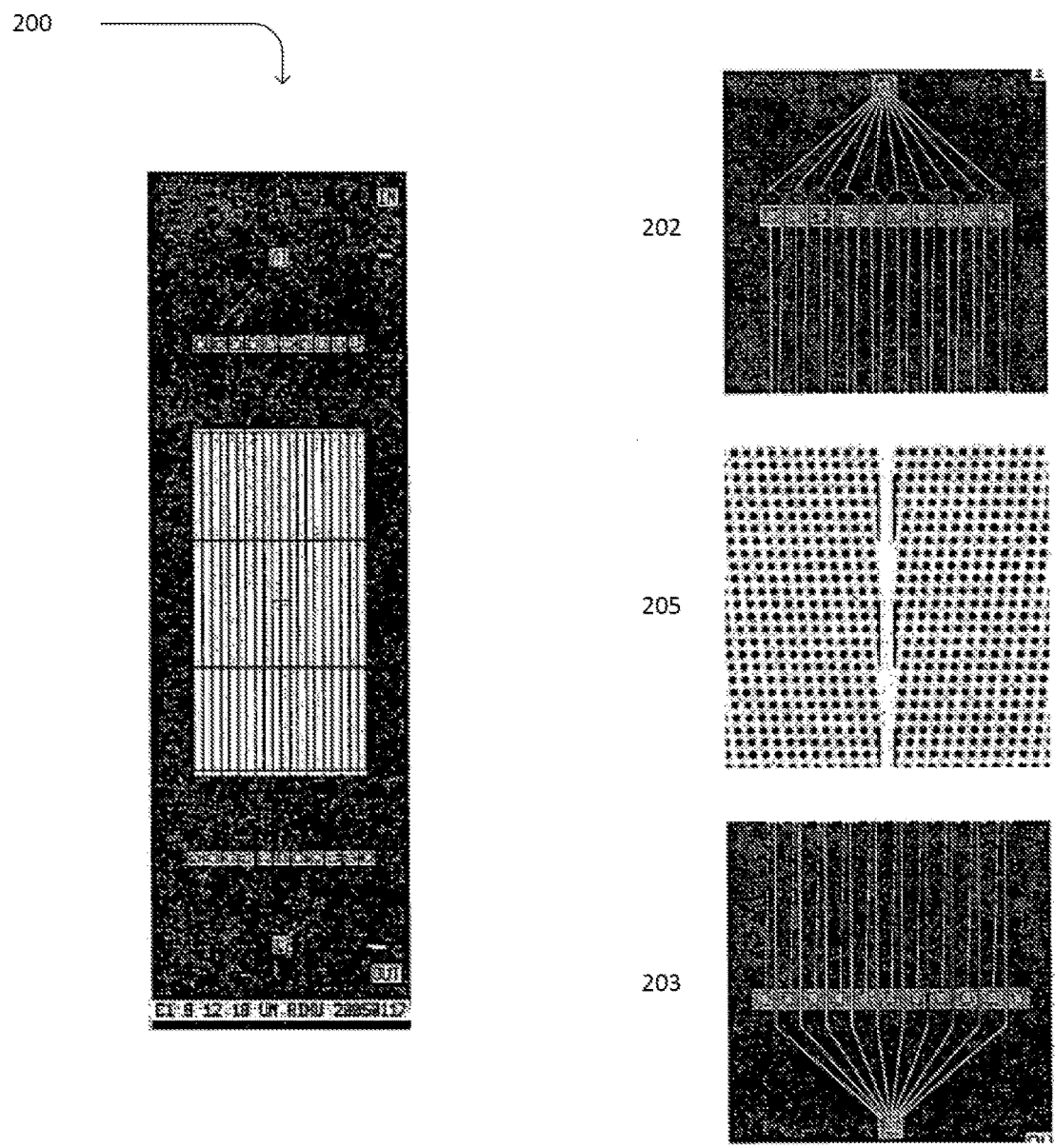
FIG. 2A is a schematic diagram of one embodiment of a debulking chip.

As shown in FIG. 2A, the first stage system can be manufactured on a single chip 200. In some embodiments, the chip can include an inlet 202, one or more arrays of microposts 205 (two in the present figure), and an outlet 203.

Figure 2B:
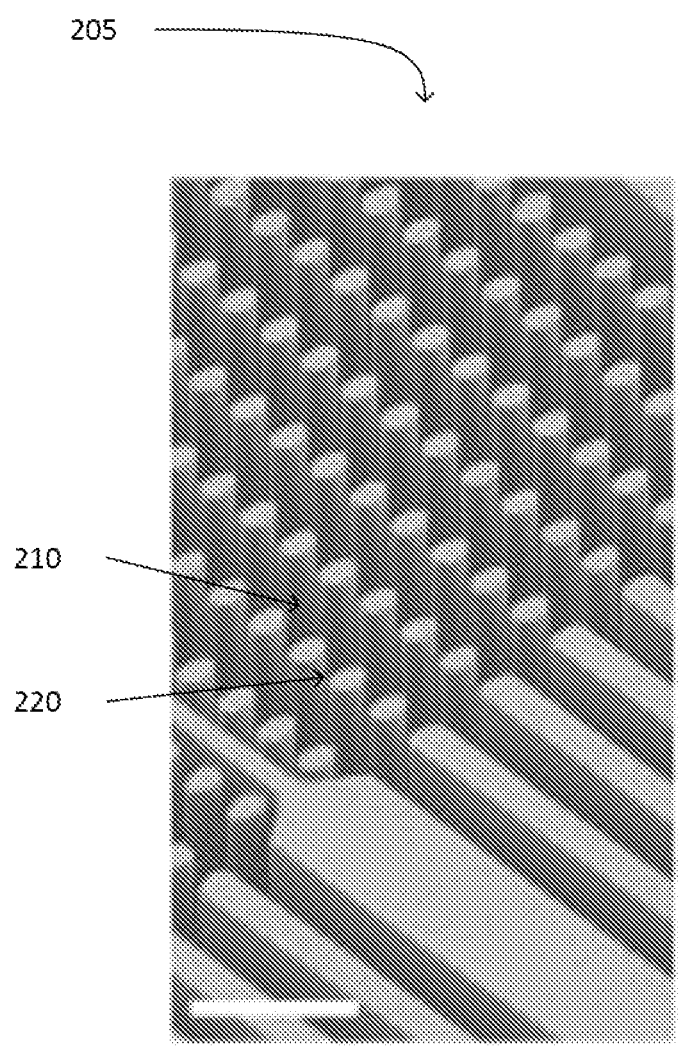
FIG. 2B is a schematic diagram of one embodiment of the micropost array on the debulking chip.

As shown in FIG. 2B, the first stage in the system can be a hydrodynamic sorting device for the separation of cells using an array of microposts 205 that selectively allow passage of particles based on their size, shape, or deformability. The size, shape, or deformability of the spaces in the array of microposts determines the types of cells that can pass through the array. Two or more arrays of microposts can be arranged in series or parallel, e.g., to remove cells of increasing size successively. For a description of such microfluidic systems, see, e.g., U.S. Pat. Nos. 8,986,966, 8,585,971 and Ozkumur et al. (2013), supra.

A variety of micropost 210 sizes, geometries, and arrangements can be used in the devices described herein. Different shapes of microposts, e.g., those with circular, square, rectangular, oval, or triangular cross sections, can be used. The size of the gaps 220 between the microposts and the shape of the microposts can be optimized to ensure fast and efficient separation. For example, the size range of the RBCs is on the order of 5-8 µm, and the size range of platelets is on the order of 1-3 µm. The size of all WBCs is greater than 10 µm. Taking these dimensions into consideration, while larger gaps between the microposts increase the rate at which the RBCs and the platelets pass through the array, increased gap size also increases the risk of losing WBCs. Smaller gap sizes ensure more efficient capture of WBCs, but also a slower rate of passage for the RBCs and platelets. Depending on the type of application different geometries can be used. For the present methods, micropost diameters of about 10 to 30 µm, e.g., about 15 to 24 µm, e.g., 10, 12, 15, 17, 20, 22, 24, 25, or 27 µm are useful. Gaps or spaces between the microposts of about 10 to 40 µm, e.g., 20 to 32 µm, e.g., 15, 20, 25, 30, 35, or 40 µm are effective.

Arrays of microposts can be manufactured by various methods. For example, an array of microposts can be formed by molding, electroforming, etching, or drilling a substrate such as a glass, a metal, or a polymer. For example, simple microfabrication techniques like poly(dimethylsiloxane) (PDMS) soft lithography, polymer casting (e.g., using epoxies, acrylics, or urethanes), injection molding, polymer hot embossing, laser micromachining, thin film surface micromachining, deep etching of both glass and silicon, electroforming, and 3-D fabrication techniques such as stereo lithography can be used for the fabrication of the channels and array of microposts of devices described herein. Most of these processes use photomasks for replication of microfeatures.

For feature sizes of greater than 5 µm, transparency based emulsion masks can be used. Feature sizes between 2 and 5 µm may require glass-based chrome photomasks. For smaller features, a glass based E-beam direct write mask can be used. The masks are then used to either define a pattern of photoresist for etching in the case of silicon or glass or define negative replicas, e.g., using SU-8 photoresist, which can then be used as a master for replica molding of polymeric materials like PDMS, epoxies, and acrylics. The fabricated channels may then be bonded onto a rigid substrate like glass to complete the device. Other methods for fabrication are known in the art and the device described herein can be fabricated from a single material or a combination of materials.

A specific first-stage hydrodynamic sorting chip was designed and fabricated deep reactive ion etching on silicon wafers. The chip was sealed with anodically bonded glass cover to form the microfluidic debulking component. A custom polycarbonate manifold was used to form the fluidic connections to the substrate and to the second-stage cell capture chamber.

Stage Two—Cell Capture Chambers

In various embodiments, the cell capture chamber can be a simple microfluidic channel that is functionalized on one or more walls and/or the floor with the platelet binding moieties, or can be more elaborate and include a mixing structure to enhance and increase the number of contacts of the platelet-associated CTCs in the sample fluid with the platelet binding moieties.

Figure 3:
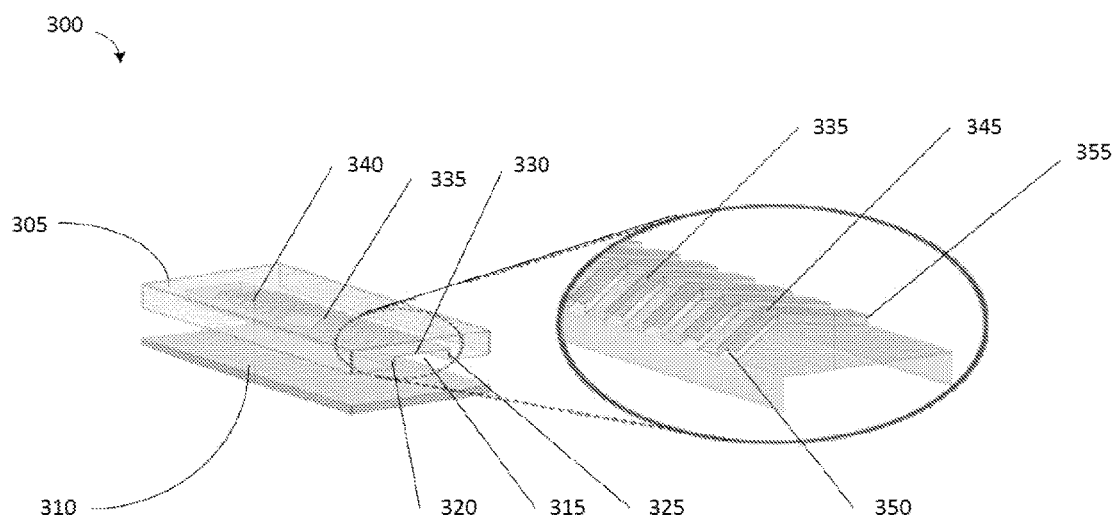
FIG. 3 is a schematic diagram of one embodiment of a microvortex "herringbone" chip.

As shown in FIG. 3, the cell capture chamber can be formed as a microvortex-generating "herringbone" chamber (or "chip") functionalized with anti-platelet antibodies for high throughput capture of platelet-associated CTCs (see e.g., PCT Application Publication No. WO 2010/036912). In this embodiment, the chamber is formed as a micro-channel formed in a microfluidic device in which grooves (or protrusions) are formed extending into (or out of) the walls of the micro-channel to create flow patterns in fluid flowing through the channel that promote interactions between any cells suspended in the fluid and the inner surfaces of the walls of the channel. The increased interactions can lead to an increase in a number of CTCs captured in the channel, and consequently, in the overall capture efficiency of the microfluidic device. In this embodiment, the capture efficiency of the microfluidic device is defined as a ratio of a number of CTCs captured in the channel and a total number of cells flowed through the channel.

The efficiency can further be increased by tailoring structural features of the microfluidic device including, for example, device substrate material, channel and groove dimensions, and the like, as well as fluid flow parameters such as flow rates based on types of particles and the types of fluids in which the particles are suspended.

An example of such a microfluidic device manufactured using soft lithography techniques is described with respect to FIG. 3. As described below, platelet-associated CTCs are captured in the micro-channel of the cell capture chamber by forming grooves in one or more of a wall, floor, and/or ceiling of the micro-channel, coating the platelet binding moieties on the inner surfaces of the walls, floor, and/or ceiling of the micro-channel, and flowing the sample fluid through the micro-channel.

FIG. 3 illustrates a microfluidic device 300 having grooves 335, 340 extending into an upper wall (or ceiling) of a channel 315 of the device 300. In some embodiments, the cell capture chambers include protrusions extending outward from the wall (e.g., V-shaped protrusions) rather than grooves extending into a wall of the channel 315. In some embodiments, a symmetric groove 335 includes two arms, each spanning a length between a first end 350 and the apex 345, and a second end 355 and the apex 345. In the illustrated embodiments, the angle α between the two arms is 90°. In some embodiments, the angle α between the arms ranges between 10° and 170°. In some implementations, a microfluidic device 300 can include an upper substrate 305 bonded to a lower substrate 310, each of which can be fabricated using an appropriate material. For example, the upper substrate 305 can be fabricated using an elastomer such as, for example, polydimethylsiloxane (PDMS), and the lower substrate can be fabricated using glass, PDMS, or another elastomer.

Alternatively, or in addition, the substrates can be manufactured using plastics such as, for example, polymethylmethacrylate (PMMA), polycarbonate, cyclic olefin copolymer (COC), and the like. In general, the materials selected to fabricate the upper and lower substrates can be easy to manufacture, for example, easy to etch, and can offer optical properties that facilitate ease of testing, for example, can be optically clear, and can be non-toxic so as to not negatively affect the cells attached to the substrate. In addition, the materials are preferred to exhibit no or limited auto-fluorescence. Further, the materials can be easy to functionalize so that analytes can be attached to the substrate. Furthermore, the materials can be mechanically strong to provide strength to the microfluidic device 300. The upper substrate 305 can be securely fastened to the lower substrate 310, with a micro-channel formed between them, as described below.

In some implementations, the micro-channel 315 can have a rectangular cross-section including two side walls 320 and 325, and an upper wall 330 formed in the upper substrate 305. Terms of relative location such as, for example, "upper" and "lower" are used for ease of description and denote location in the figures rather than necessary relative positions of the features. For example, the device can be oriented such that the grooves are on a bottom surface of the channel or such that a central axis of the channel extends vertically. Alternatively, the cross-section of the micro-channel 315 can be one of several shapes including but not limited to triangle, trapezoid, half-moon, and the like. The lower substrate 310 can form the lower wall of the micro-channel 315 once bonded to the upper substrate 305. In some implementations, the micro-channel 315 includes multiple grooves 335 formed in the upper wall 330 of the micro-channel 315. Alternatively, the grooves 335 can be formed in any of the walls, and/or can be formed in more than one wall of the micro-channel 315. The grooves 335 can span an entire length of a wall, or only a portion of the wall.

Figure 4:
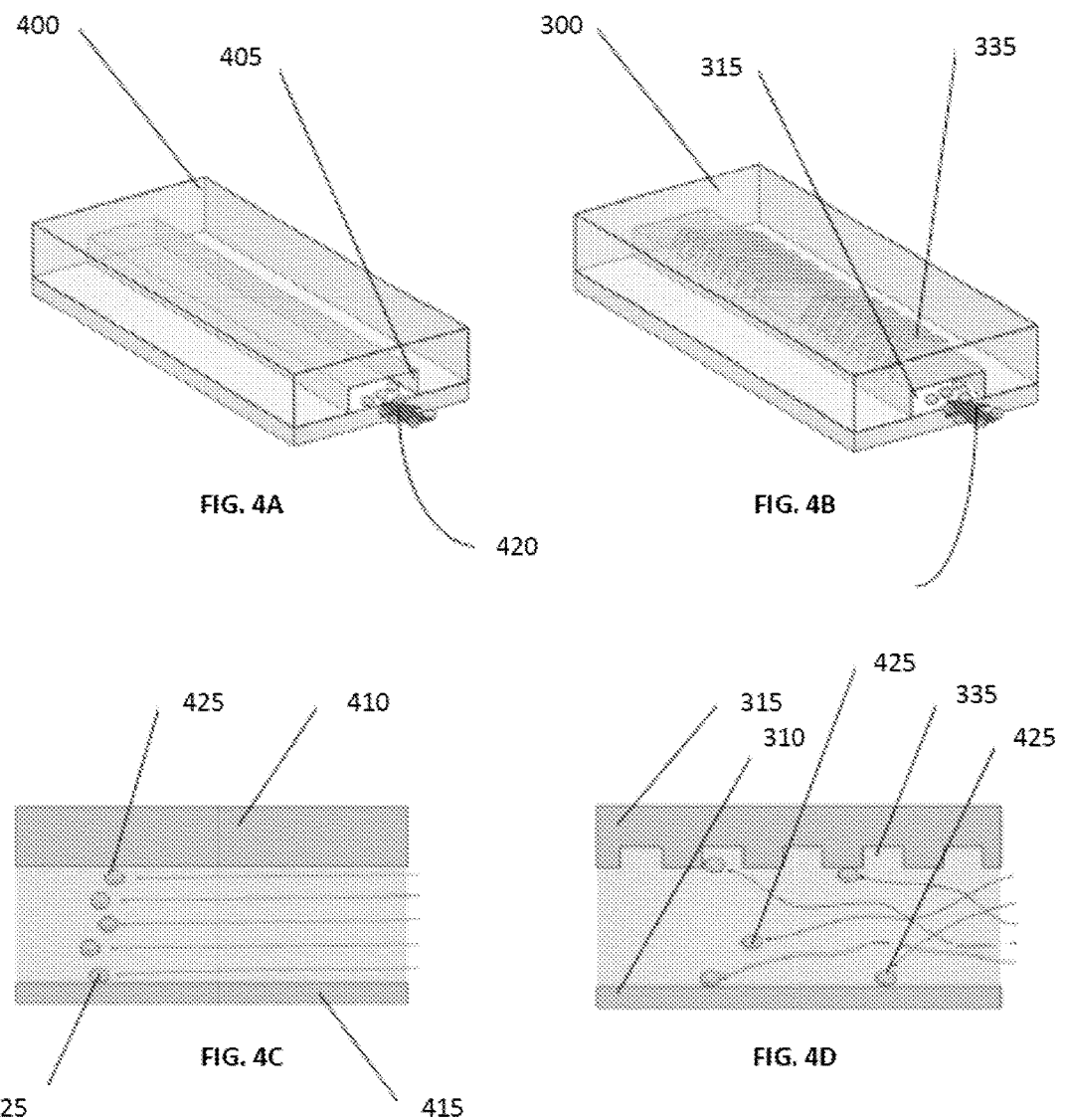
FIGS. 4A to 4D are a series of schematic diagrams of a flow pattern of particles, e.g., cells or clusters of cells, flowing through the microvortex "herringbone" chip of FIG. 3.

FIGS. 4A-4D are schematics illustrating particle suspensions flowing through a micro-channel having flat walls and another micro-channel having grooves formed in a wall. FIG. 4A shows a microfluidic device 400 that includes a micro-channel 405 having a rectangular cross-section. The walls of the micro-channel 405 do not include grooves such as those described with respect to the microfluidic device 300, i.e., surfaces of the walls are flat. A particle suspension including platelet-associated target cells 425 suspended in a fluid is illustrated flowing through the micro-channel 405. In contrast, FIG. 4B shows a similar suspension flowing through the microfluidic device 300.

As the fluid flows past a herringbone pattern formed by arranging grooves 335 in a column in the micro-channel 315, the grooves 335 in the path of the fluid disrupt fluid flow. In some embodiments, depending upon flow velocity and the dimensions of the grooves, specifically, for example, a size of the grooves and an angle between the two arms of a groove, the disruption in the fluid flow leads to a generation of microvortices in the fluid. The microvortices are generated because the grooves induce fluid flow in a direction that is transverse to a principal direction of fluid flow, i.e., the axial direction. In some embodiments, although microvortices are not generated, the grooves 335, 340 induce sufficient disruption to alter the flow path of portions of the fluid to increase wall-particle interactions.

Without any grooves, as shown in FIG. 4C, the platelet-associated target cells 425 suspended in the fluid travel through the flat micro-channel 405 in a substantially linear fashion such that only those particles 425 near the edges of the flow field (e.g., immediately adjacent to the walls of the micro-channel 405) are likely to interact with antibodies bound to the micro-channel 205 walls. In contrast, as shown in FIG. 4D, flowpaths of the platelet-associated target cells 425 traveling past the herringbone groove patterns experience disruption by the microvortices in the fluid, increasing the number of interactions between the cells and the antibodies bound to the walls and/or grooves. The microvortices are affected by the structural features of each groove 335 formed in the upper wall 315 of the microfluidic device 300.

The second-stage herringbone chips can be made of PDMS bonded to glass substrates using soft lithography techniques as previously described. The chip surface can then be functionalized with anti-CD41 antibody (Abcam) using avidin-biotin chemistry.

The first-stage hydrodynamic sorting chip and the second-stage herringbone chip can be manufactured on a single chip, or can be manufactured as separate chips and connected by a conduit, such as plastic or other tubing.

EXAMPLES

The invention is further described in the following examples, which do not limit the scope of the invention described in the claims.

Example 1—CTC Isolation from Clinical Samples

The present methods were tested to determine their efficacy in isolating CTCs from different types of cancers.

Patients with advanced lung, breast, and melanoma cancer were recruited according to a protocol approved by the institutional review board (IRB). All specimens were collected into Vacutainer® (Becton-Dickinson) tubes containing the anticoagulant EDTA and were processed through the microfluidic chips within 4 hours of blood draw. Additional platelet inhibitors, such as theophylline, adenosine, dipyridamole, Argatroban and prostaglandin I2, were added immediately after blood collection. Fixed blood samples were collected directly in Cyto-Chex® BCT tubes (Streck).

Samples were run on a two-stage microfluidic system described above. In particular, the first-stage hydrodynamic sorting chips were fabricated with deep reactive ion etching on silicon wafers. The chip was sealed with anodically bonded glass cover to form the microfluidic chamber. A custom polycarbonate manifold was used to form the fluidic connections to the microchip. We tested two different array configurations with gaps between microposts of 20 or 32 µm. An array with 20-µm gaps retains virtually all nucleated cells with minimal contaminating RBCs, but has a cutoff for cells larger than 21 µm and may therefore lose large CTCs or CTC clusters. In contrast, an array with 32-µm gaps has an extended operating range for cells between 8 and 30 µm but retains only 60% of WBCs. Because the cells lost in the 32-µm gap array are granulocytes and lymphocytes that are smaller than the reported CTC sizes, we selected this array for the CTC isolation system.

The second-stage herringbone chips were made of PDMS bonded to glass substrates using soft lithography techniques as previously described above. The chip surface was functionalized with anti-CD41 antibody (Abeam) using avidin-biotin chemistry.

Figure 5:
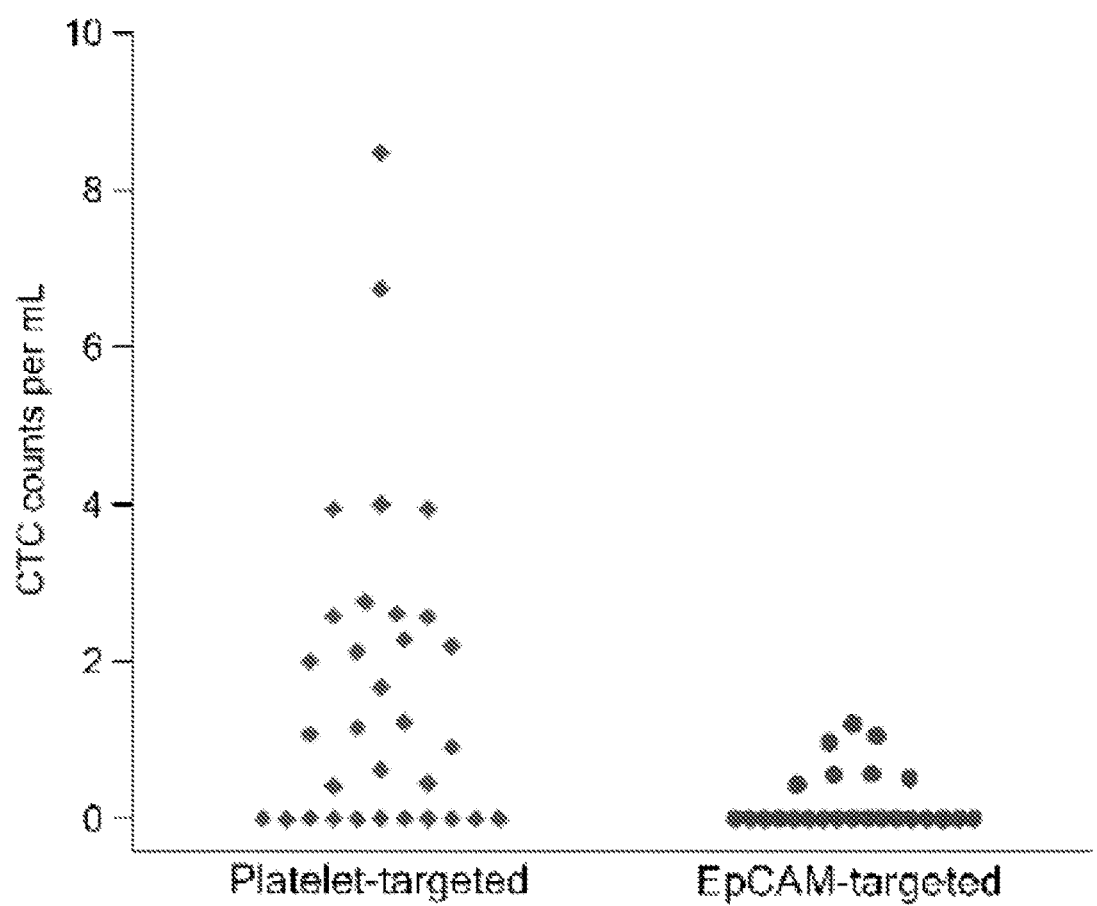
FIG. 5 is a graph showing CTC counts of blood samples from metastatic lung patients that were captured with EpCAM and CD41 antibodies, respectively.

The results are shown in FIG. 5 in the form of a graph showing (on the left-hand side) CTC counts of 32 blood samples from metastatic lung patients that were captured with EpCAM and CD41 antibodies respectively. All cells captured on the chip were processed with a four-color staining assay for simultaneous CTC identification and platelet characterization. The captured cells that were positive for tumor markers (EpCAM, cadherin-11) and DAPI while negative for the hematopoietic markers (CD45) were scored as CTCs. Reliable CTC capture has been achieved in 21 of 32 cases (66%), with counts ranging from 0.4 to 8.5 CTCs/mL.

In comparison, in-parallel CTC capture on microfluidic devices functionalized with EpCAM antibodies revealed consistently lower positive hits (FIG. 5, right hand side). The higher CTC counts from platelet-targeted approach are due to the capability of the present methods to capture lung CTCs that might lose their epithelial nature thus difficult to target by EpCAM antibodies.

The platelets were stained by CD61 antibodies to characterize their distribution around CTC surface. The CTCs captured using the new system exhibit a wide range of platelet coverage, including a subpopulation of CTCs that were completely coated with platelets/fibrin. These platelet-covered CTCs have been hypothesized as high metastatic potential precursors because of platelet-enhanced tumor-cell survival and proliferation, but are very difficult to capture by conventional positive selection methods targeting tumor surface antigens. Thus, the new systems and methods provide a new and improved technique to capture these CTCs.

Example 2—Isolation of Different Types of Cancers

The microfluidic platform was extended to isolate CTCs from different types of cancer patients with both epithelial (breast) and non-epithelial (melanoma) tumor origins. The breast CTCs were identified with the same protocol as lung patient samples, while melanoma CTCs were stained with an antibody cocktail that targets melanoma specific antigens (CSPG4, MCAM, TYRP1, and α-SMA) as previously reported. Preliminary results have demonstrated reliable CTC capture for both cancer types (3 of 5 cases for breast sample, counts ranging from 0.9 to 2.7 CTC/mL; 5 of 6 cases for melanoma sample, counts ranging from 1.4 to 17 CTC/mL). Similar to the lung cancer results, all the CTCs captured with current approach are associated with different extent of platelet coverage.

As discussed above, the lung and breast CTCs were identified with EpCAM/Cadherin-11 (green) as epithelial and mesenchymal markers, while the melanoma CTCs were stained with a cocktail of CSPG4, MCAM, TYRP1, and α-SMA (green) antibodies. WBCs and platelets were stained with CD45 (red) and CD61 (gold) respectively. Microscope imaging clearly showed each type of CTC was captured (results not shown).

Thus, the system tested is capable of reliable capture of CTCs in the form of single cells or clusters from metastatic cancer patients with both epithelial (lung, breast) and non-epithelial (melanoma) tumor origins. These results indicate that the platelet-targeted capture of CTCs is effective for multiple types of cancer.

Example 3—Anticoagulant and CTC Purity

A key issue that potentially limits the performance of the platelet-targeted approach is the relatively low purity of CTCs compared with other technologies. A large number of contaminating WBCs ($>10^5$/mL) has been observed on chip, making the downstream analysis very challenging. Staining with platelet-specific antibodies revealed that most of the captured WBCs were also coated with platelets. The formation of these so-called platelet-leukocyte aggregates (PLAs) originates from spontaneous platelet activation and the consequent expression of p-selectin, which will then bind to PSGL-1 receptors on leukocyte surface. PLAs are not removed by size-based sorting, and are captured by anti-platelet antibodies together with platelet-associated CTCs.

Figure 7:
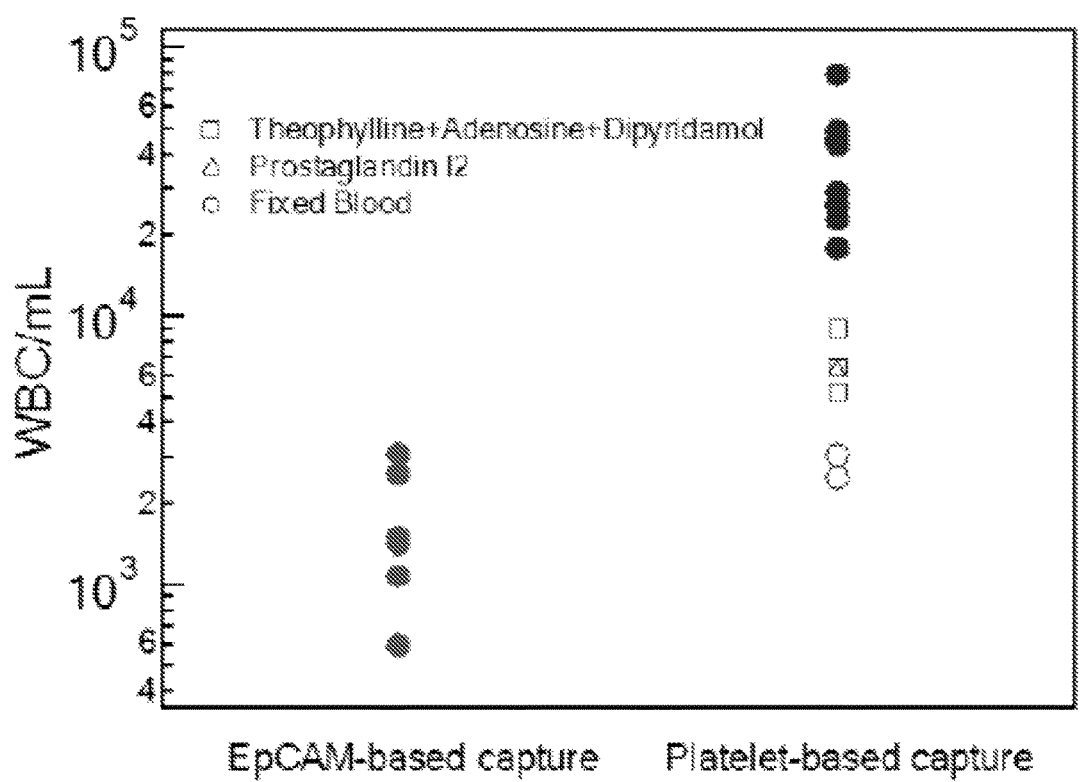
FIG. 7 is a graph showing reduced platelet-leukocyte aggregate formation with the addition of EDTA and prostaglandin I2.

To reduce WBC contamination and improve CTC purity, we tested a variety of platelet inhibitors, such as theophylline, adenosine, dipyridamole, Argatroban and prostaglandin I2, for blood stabilization. EpCAM-based capture was used as a control to evaluate the number of WBCs per mL of blood sample. These results are shown on the left column of FIG. 7. EpCAM-based capture generally resulted in less WBC contamination, though this method of CTC isolation suffers from a number of deficiencies discussed above. Platelet-based capture was tested using a variety of platelet inhibitors, with the results shown in the right column of FIG. 7 (filled in circles represent untreated samples. The combination of EDTA with prostaglandin I2 (shown as open triangles on the graph) was found to be effective in inhibiting the PLA formation, and reduced the number of contaminating WBCs by 90% (FIG. 7).

To completely inhibit the PLA formation, the blood sample was fixed in Cyto-Chex® BCT tubes for 24 hours before processing, which yielded the best CTC purity for platelet-based capture. These samples were referred to "fixed blood" (open circles).

Figure 8A:
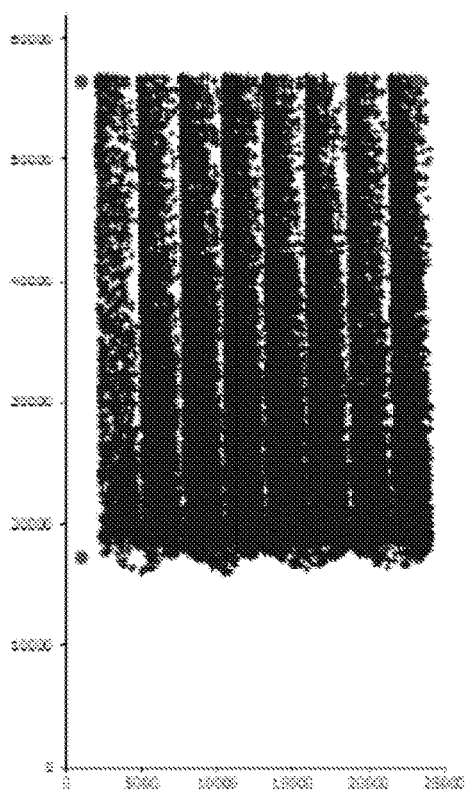
FIGS. 8A and 8B are heat maps of WBCs captured on a microvortex "herringbone" chip for non-treated (8A) and prostaglandin I2-treated (8B) blood samples.
Figure 8B:
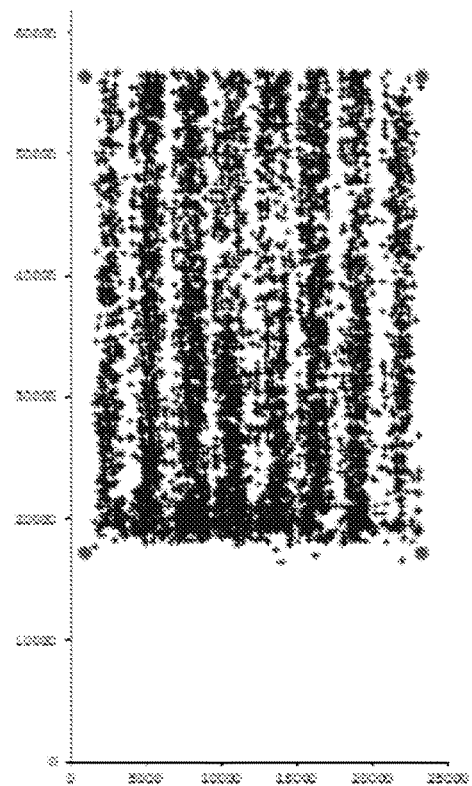

FIGS. 8A and 8B show heat maps of microfluidic devices containing individual captured WBCs (dark spots) mapped to their relative position on the microfluidic device. There was a strong decay pattern with the majority of captured cells positioned at the inlet of the device with untreated blood samples, suggesting specific interaction between WBCs and CD41 antibodies through surface platelets (FIG. 8A). In contrast, heat maps of prostaglandin I2-treated blood samples displayed significantly fewer captured cells, distributed randomly throughout the device (FIG. 8B).

Furthermore, by gently fixing the blood sample with commercial available blood stabilization solutions (e.g., Cyto-Chex® BCT tube from Streck), PLA formation can be mostly suppressed during processing because of the complete platelet deactivation, giving rise to substantially improved CTC purity that is comparable to the conventional EpCAM-targeted capture. The CTC capture was not affected in these studies as the TCIPA occurred under in-vivo conditions and those platelet-associated aggregates were already formed before blood collection.

This solution to platelet-WBC aggregates improves the results of the two-stage microfluidic platform designed to achieve platelet-targeted CTC capture.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:
1. A method for isolating platelet-associated nucleated target cells from a sample fluid, the method comprising:
   obtaining a cell capture chamber comprising a plurality of binding moieties bound to one or more walls of the chamber, wherein the binding moieties specifically bind to platelets;
   flowing the sample fluid through the cell capture chamber under conditions that allow the binding moieties to bind to any platelet-associated nucleated target cells in the sample fluid to form complexes; and
   separating and collecting platelet-associated nucleated target cells from the complexes thereby isolating the platelet-associated nucleated target cells from the sample fluid.
2. The method of claim 1, wherein the platelet-associated nucleated target cells comprise any one or more of circulating epithelial cells, circulating tumor cells (CTCs), circulating endothelial cells (CECs), circulating stem cells (CSCs), neutrophils, and macrophages.

3. The method of claim 1, further comprising treating the sample fluid with a platelet inhibitor prior to flowing the sample fluid through the cell capture chamber, wherein the platelet inhibitor inhibits unbound platelets from adhering to other platelets, red blood cells, and white blood cells.

4. The method of claim 3, wherein the platelet inhibitor comprises theophylline, adenosine, dipyridamole, Argatroban, or prostaglandin I2.

5. The method of claim 1, wherein the binding moieties comprise antibodies that bind specifically to platelets.

6. The method of claim 1, further comprising selectively depleting unbound platelets from the sample fluid while maintaining platelet-associated nucleated target cells in the sample fluid before flowing the sample fluid through the cell capture chamber.

7. The method of claim 6, wherein the platelet depletion is performed in a microfluidic device comprising a channel containing an array of microposts to implement deterministic lateral displacement.

8. The method of claim 6, wherein the platelet depletion is performed in a microfluidic device using centrifugal or inertial forces, or both.

9. The method of claim 7, wherein the cell capture chamber and the microfluidic device are both located on a single substrate.

10. The method of claim 1, wherein the binding moieties are bound to nanostructures that comprise a first member of a binding pair, wherein one or more internal surfaces of the cell capture chamber are bound to a layer of gelatin functionalized with a plurality of second members of the binding pair, and wherein the nanostructures are bound to a top layer of the gelatin by a binding interaction of the first and second members of the binding pair.

11. The method of claim 10, wherein the platelet-associated nucleated target cells are bound to the nanostructures by the binding moieties and the platelet-associated nucleated target cells are isolated by releasing the nanostructures from the gelatin by melting the gelatin at an increased temperature.

12. The method of claim 10, wherein the platelet-associated nucleated target cells are bound to the nanostructures by the binding moieties and the platelet-associated nucleated target cells are isolated by releasing the nanostructures from the gelatin by applying a localized shear stress to the gelatin layer.

13. The method of claim 10, wherein the platelet-associated nucleated target cells are bound to the nanostructures by the binding moieties and the platelet-associated nucleated target cells are isolated by releasing the nanostructures from the gelatin by a light-targeted photothermal effect.

14. The method of claim 1, wherein the platelet-associated nucleated target cells are circulating tumor cells (CTCs).

15. The method of claim 1, wherein the sample fluid comprises blood, bone marrow, plural effusions, or ascites fluid.

16. A two-stage microfluidic system for isolating platelet-associated nucleated target cells from a sample fluid, the system comprising:
a first chamber comprising
a microchannel having an inlet, a waste outlet, a product outlet, and an array of microposts arranged between the inlet and the waste and product outlets, wherein the microposts are arranged in rows and spaced apart by a distance that enables red blood cells and unbound platelets to flow through the device to the waste outlet and to cause platelet-associated nucleated target cells to be laterally displaced by the array of microposts to the product outlet, wherein the microposts in each subsequent row are offset laterally from microposts in a previous row by a distance less than the spacing between the microposts within the row;
a second chamber comprising
a microchannel having an inlet and an outlet, wherein sample fluid flows from the inlet to the outlet through the microchannel, and a plurality of grooves defined in and arranged on an internal surface of one or more walls, floor, and ceiling of the microchannel to create microvortices within the sample fluid; and binding moieties fixed to at least one of the internal surfaces of the microchannel, wherein the binding moieties specifically bind to platelets; and
a conduit fluidly connecting the product outlet of the first chamber to the inlet of the second chamber.

17. The system of claim 16, wherein the microposts are spaced apart within a row by a distance of about 30 microns to about 60 microns, and subsequent rows are spaced apart from a previous row by a distance of about 5 microns to about 15 microns.

18. The system of claim 16, wherein the first chamber and the second chamber are both located on a single substrate.

19. The system of claim 16, wherein the grooves include an apex and two arms connected to the apex to form a V-shape, and wherein the grooves are arranged such that the sample fluid flows past the arms towards the apex.

20. The system of claim 16, wherein the binding moieties are bound to nanostructures that comprise a first member of a binding pair, wherein one or more internal surfaces of the microchannel of the second chamber are bound to a layer of gelatin functionalized with a plurality of second members of the binding pair, and wherein the nanostructures are bound to a top layer of the gelatin by a binding interaction of the first and second members of the binding pair.

* * * * *